(12) United States Patent
Shibata et al.

(10) Patent No.: US 9,789,525 B2
(45) Date of Patent: Oct. 17, 2017

(54) DEVICE AND METHOD FOR DETECTING FINAL DEPTH OF PUNCH IN MACHINE TOOL

(71) Applicant: AMADA COMPANY, LIMITED, Kanagawa (JP)

(72) Inventors: Takahiro Shibata, Kanagawa (JP); Yingjun Jin, Kanagawa (JP); Junichi Koyama, Kanagawa (JP)

(73) Assignee: AMADA COMPANY, LIMITED, Kanagawa (JP)

( * ) Notice: Subject to any disclaimer, the term of this patent is extended or adjusted under 35 U.S.C. 154(b) by 268 days.

(21) Appl. No.: 14/437,067

(22) PCT Filed: Oct. 23, 2013

(86) PCT No.: PCT/JP2013/078708
§ 371 (c)(1),
(2) Date: Apr. 20, 2015

(87) PCT Pub. No.: WO2014/065325
PCT Pub. Date: May 1, 2014

(65) Prior Publication Data
US 2015/0246382 A1 Sep. 3, 2015

(30) Foreign Application Priority Data

Oct. 23, 2012 (JP) .................... 2012-233728
Oct. 22, 2013 (JP) .................... 2013-218951

(51) Int. Cl.
*G06F 19/00* (2011.01)
*B21D 5/00* (2006.01)
(Continued)

(52) U.S. Cl.
CPC ............. *B21D 5/006* (2013.01); *B21D 5/02* (2013.01); *G01N 3/20* (2013.01); *G06F 15/00* (2013.01); *G06F 19/00* (2013.01)

(58) Field of Classification Search
CPC . B21D 5/01; B21D 5/006; B21D 5/02; G01N 3/20; G06F 15/00; G06F 19/00
(Continued)

(56) References Cited

U.S. PATENT DOCUMENTS 4,408,471 A  10/1983  Gossard et al.
4,797,831 A *  1/1989  Dressing ................ B30B 15/20
                                              700/165

(Continued)

FOREIGN PATENT DOCUMENTS

JP    6-134524    5/1994
JP    8-24955     1/1996
(Continued)

OTHER PUBLICATIONS

Search report from PCT/JP2013/078708, dated Jan. 28, 2014.
Supplemental European Search report for European Patent Application No. 13849293.9, dated Jun. 21, 2016.

*Primary Examiner* — David B Jones
(74) *Attorney, Agent, or Firm* — Greenblum & Bernstein, P.L.C.

(57) ABSTRACT

A machine tool for bending a workpiece by clamping the workpiece with a die and a punch is configured to: distinguish a material characteristic of the workpiece as an actual value and a nominal value; determine an actual material characteristic during an machining operation and re-calculate an operation target value suitable for the workpiece; and bend the workpiece by operating the punch in accordance with the suitable operation target value thus re-calculated.

4 Claims, 9 Drawing Sheets

(51) Int. Cl.
  *G06F 15/00*  (2006.01)
  *B21D 5/02*  (2006.01)
  *G01N 3/20*  (2006.01)

(58) Field of Classification Search
  USPC .......................................................... 72/380
  See application file for complete search history.

(56) References Cited

U.S. PATENT DOCUMENTS

| | | | |
|---|---|---|---|
| 5,027,631 A * | 7/1991 | Naito | B21D 28/002 |
| | | | 700/160 |
| 5,813,263 A | 9/1998 | Tokai | |
| 5,857,366 A * | 1/1999 | Koyama | B21D 5/004 |
| | | | 72/17.3 |
| 7,079,919 B2 * | 7/2006 | Gerritsen | B21D 5/02 |
| | | | 100/43 |
| 2003/0015011 A1 | 1/2003 | Koyama et al. | |
| 2004/0111177 A1 | 6/2004 | Gerritsen et al. | |
| 2006/0117824 A1 | 6/2006 | Takehara et al. | |

FOREIGN PATENT DOCUMENTS

| | | |
|---|---|---|
| JP | 2000-140943 | 5/2000 |
| JP | 2001-198622 | 7/2001 |
| JP | 2009-119522 | 6/2009 |
| WO | 02/074463 | 9/2002 |

* cited by examiner (a)

(b)

DEVICE AND METHOD FOR DETECTING FINAL DEPTH OF PUNCH IN MACHINE TOOL

TECHNICAL FIELD

The present invention relates to a device and a method for detecting the final depth of a punch in a bending machine configured to bend a workpiece, the final depth being a position at which the bending starting from a pinch position finishes. The present invention relates particularly to a punch final depth detection device and a punch final depth detection method which, even when material characteristics vary from one workpiece to another, are capable of accurately bending a workpiece by correcting a reference depth of the punch in accordance with the variation in the material characteristics of the workpiece.

BACKGROUND ART

Generally, conventional machine tools such as bending machines for bending a plate-shaped workpiece (material) are configured to the bending by: detecting a pinch position (the position of the upper surface of the workpiece) at which the workpiece is clamped with a die and a punch; calculating a punch final depth as a position at which the bending starting from the detected pinch position finishes, based on the pinch position; and pushing in the punch to the punch final depth.

Note that the depth of the punch and the bend angle of the workpiece are closely related. To accurately bend the workpiece at a given angle, it is important to obtain an accurate punch final depth.

As this type of technique, those described in literatures listed below have heretofore been known, for example (Japanese Patent Application Publication Nos. Hei 6-134524, 2000-140943, and Hei 8-24955).

SUMMARY OF INVENTION

Technical Problems

Meanwhile, workpieces to be machined have workpiece deformation characteristics such as thickness and material constant, and these workpiece deformation characteristics vary from one workpiece to another. This leads to a problem of accuracy error due to which the bend angle differs from one workpiece to another even if the workpieces are bent by a calculated depth.

In the conventional practice, when the bend angle is not stable like the above case, the operator checks the accuracy after the machining and corrects the final depth via feedback to a NC device each time an error is found. This imposes a large burden on the operator and lowers the efficiency of the operation.

Moreover, in the conventional practice, tensile tests have been conducted to study material characteristics in the plastic deformation region as workpiece deformation characteristics.

However, these tensile tests involve cutting off a test piece in accordance with the specifications, measuring the thickness with a micrometer gauge, attaching a strain gauge, and using a tensile tester. Thus, the tensile tests require a large amount of time and effort and a costly apparatus.

Moreover, as a conventional method for measuring the material characteristics during machining, there has been material characteristic prediction with an influence coefficient using shear processing.

However, if the material characteristics of individual blank materials detected in shear processing are to be used in bending, individual management of each blank material is necessary. This leads to a problem of complicated management.

The present invention has been made in view of the above, and an object thereof is to provide a punch final depth detection device and a punch final depth detection method which, even when the material characteristics vary from one workpiece to another, are capable of accurately bending a workpiece by correcting the final depth of the punch in accordance with the variation in the material characteristics of the workpiece.

In order to solve the problem, a feature of the present invention is a machine tool configured to bend a workpiece by clamping the workpiece with first and second bending tools, wherein
as preparation, the machine tool
(1) obtains a relationship between stress and strain of each of a plurality of kinds of workpieces by performing a material test thereon,
(2) obtains a relationship between strain and machining load at a particular portion of each of the workpieces by calculating a machining model which is based on the workpiece with use of the relationship between the stress and the strain, and
(3) further calculates a relational equation of the machining load and stress of the workpiece which are not dependent on a material thereof, and
thereafter, the machine tool obtains, as a material constant, a relationship between stress and strain of the workpiece to be bent based on the relational equation of the machining load and the stress and values of the strain and machining load of the workpiece to be bent.

Another feature of the present invention is that the machine tool further
calculates a final position of the second bending tool in the bending of the workpiece based on the material constant and a machining condition, and
bends the workpiece based on the final position of the second bending tool.

Another feature of the present invention is that the step of obtaining the relationship between the stress and the strain of the workpiece to be bent as the material constant includes:
setting a reference position of the second bending tool;
measuring the strain at the particular portion and the machining load during the bending operation; and
calculating a material constant which is based on the relationship between the stress and the strain of the workpiece to be bent, from the measured values of the strain at the particular portion and the machining load and an approximate equation of the relationship between the machining load and the stress of the workpiece.

Another feature of the present invention is that the step of obtaining the relationship between the stress and the strain of the workpiece to be bent as the material constant includes:
setting a reference position of the second bending tool;
measuring a stroke and the machining load during the bending operation;
obtaining a value of the strain at the particular portion of the workpiece to be bent from a stroke-strain conversion equation; and
calculating the material constant which is based on the relationship between the stress and the strain of the workpiece to be bent, from values of the strain at the particular portion and the machining load and an approximate equation of the relationship between the machining load and the stress of the workpiece.

Another feature of the present invention is that a machine tool configured to bend a workpiece by clamping the workpiece with first and second bending tools:

distinguishes a material characteristic of the workpiece as an actual value and a nominal value;

determines an actual material characteristic during an machining operation and re-calculates an optimal operation target value for the workpiece; and bends the workpiece by operating any one of the first bending tool and the second bending tool in accordance with the optimal operation target value thus re-calculated.

DESCRIPTION OF EMBODIMENTS

Hereinbelow, embodiments carrying out the present invention will be described by using the drawings.

Figure 1:
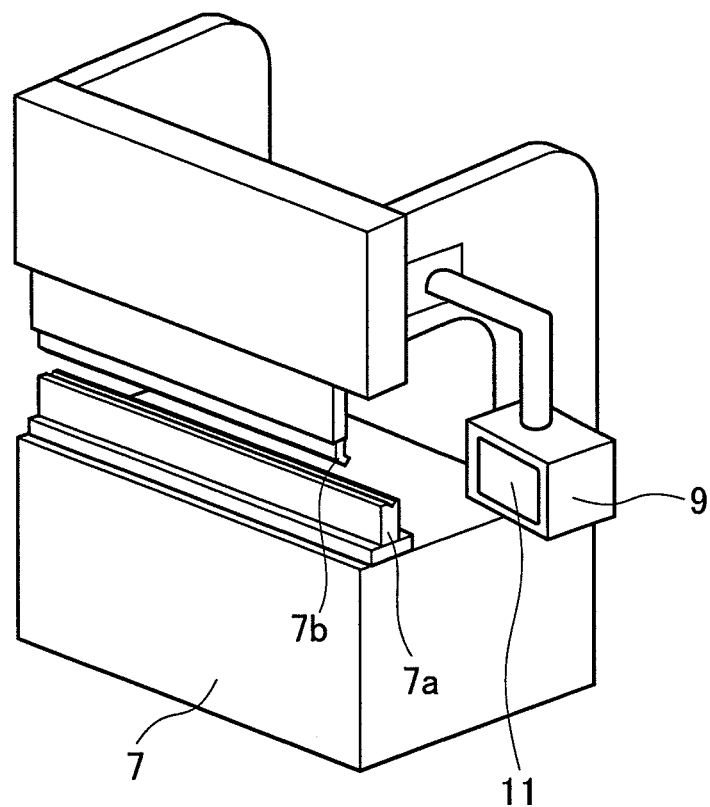
FIG. 1 is an explanatory view schematically showing a machine tool (bending machine) carrying out the present invention.
Figure 2:
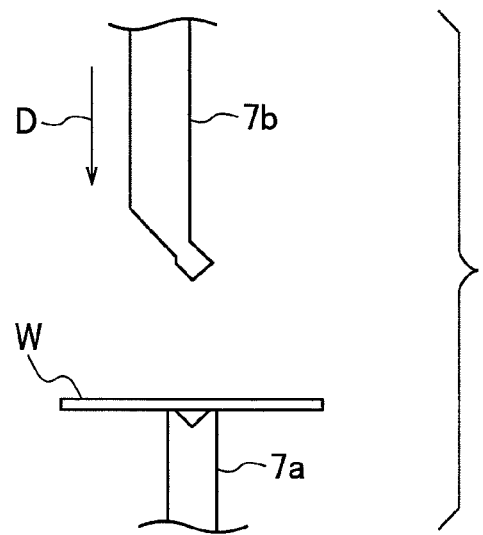
FIG. 2 is a schematic view of a part around a die and a punch shown in FIG. 1.
Figure 3:
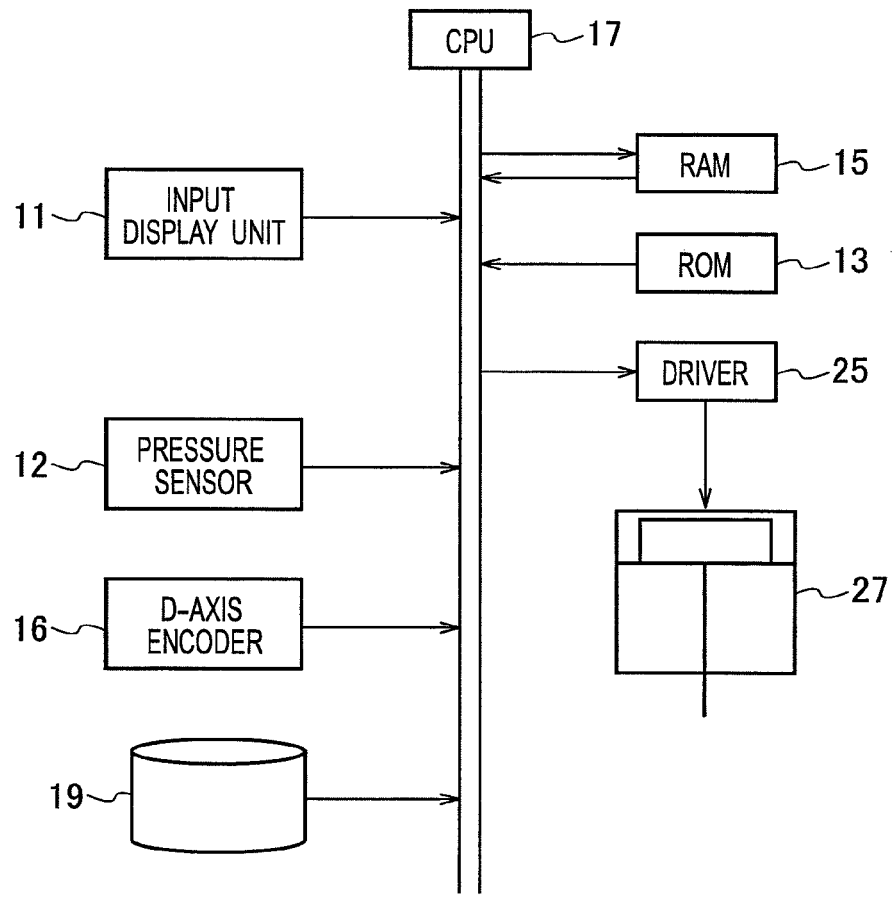
FIG. 3 is a block diagram showing the schematic configuration of a control device 9 of a bending machine 7 shown in FIG. 1.

FIG. 1 is an entire perspective view schematically showing a machine tool (first embodiment) carrying out the present invention. FIG. 2 is a schematic view of a part around a die and a punch shown in FIG. 1. FIG. 3 is a block diagram showing the schematic configuration of a control device 9 of a bending machine 7 shown in FIG. 1.

As shown in FIG. 1, this machine tool (bending machine) 7 is configured to bend a workpiece (material) fed between a die 7a and a punch 7b with the die 7a and the punch 7b by sliding the punch 7b vertically in a D-axis direction D (see FIG. 2) as shown by the arrow relative to the die 7a. The die 7a is provided to a lower part as a first bending tool, whereas the punch 7b is provided to an upper part as a second bending tool.

Moreover, as shown in FIGS. 2 and 3, this bending machine 7 is provided with: a pressure sensor 12 (shown in FIG. 3) provided to an upper portion of the punch 7b and configured to detect pressure applied to the punch 7b; and a D-axis encoder 16 (shown in FIG. 3) provided to the upper portion of the punch 7b and configured to detect the slide position of the punch 7b on the D axis.

Further, the bending machine 7 includes the control device 9 responsible for the control on the whole machine tool. This control device 9 is provided with an input-display unit 11 configured to display predetermined images and receive instructions from the operator.

Furthermore, under control of the control device 9, the workpiece is bent in accordance with bending operation inputted and set through the input-display unit 11. In this example, the final depth of the punch (the position to which the punch is finally pushed in or the final position of the punch) to be described later is detected, and the bending is performed by this corrected final depth thus detected.

This control device 9 functions also as a punch final depth detection device configured to detect the corrected final depth amount based on the result of detection by the pressure sensor 12 or D-axis encoder 16 mentioned above.

As shown in FIG. 3, the control device 9 of the bending machine 7 includes a CPU 17 to which a ROM 13 and a RAM 15 are connected through a bus, and the pressure sensor 12, the input-display unit 11 serving as both an input unit and a display unit, the D-axis encoder 16, and a database 19 are also connected to the CPU 17 through the bus.

Moreover, a driver 25 configured to drive a cylinder 27 configured to vertically drive an upper table equipped with the punch 7b is also connected to the CPU 17 through the bus.

In this example, the CPU 17 is configured to detect the final depth of the punch (the amount by which to push the punch in) as described later and also perform the inputted and set bending operation by using data on the punch and the die, data on the product shape, and data on the machining object (workpiece W) in the database 11 and also using the RAM 15 based on a computer program from the ROM 13 in accordance with settings and instructions from the operator through the input-display unit 11.

Next, the operation of the punch final depth detection device will be described with reference to FIGS. 4 and 5.

Figure 4:
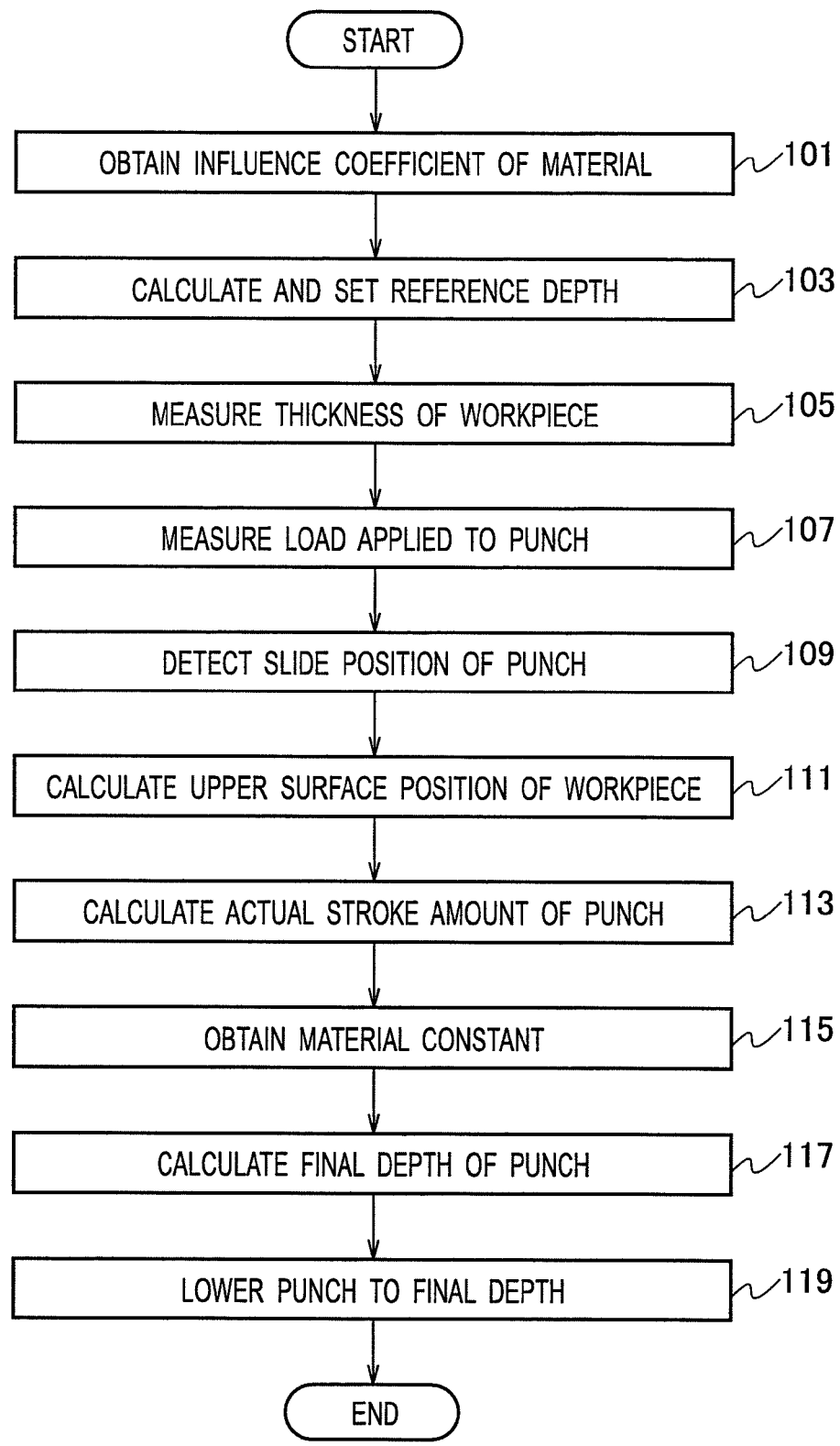
FIG. 4 is a flowchart of a punch final depth detection operation by a punch final depth detection device shown in FIG. 3.
Figure 5:
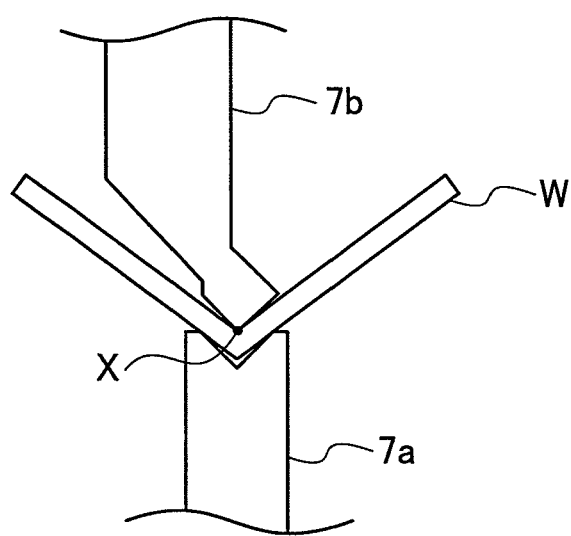
FIG. 5 is an explanatory view of the punch final depth detection operation by the punch final depth detection device shown in FIG. 3.

FIG. 4 is a flowchart of punch final depth detection operation by the punch final depth detection device shown in FIG. 3. FIG. 5 is an explanatory view of the punch final depth detection operation by the punch final depth detection device shown in FIG. 3.

Note that the CPU 17 performs this punch final depth detection operation by using the RAM 15 based on the computer program from the ROM 13 as mentioned above.

Here, to describe a final depth ST of the punch 7b, first of all, a pinch position refers to a position at which the workpiece W is clamped by the die 7a and the punch 7b.

More specifically, the pinch position is equivalent to the distance from a die original position to the lower end of the punch 7b in a state where the lower end of the punch 7b is in contact with the upper surface of the workpiece W with a thickness t placed on the die 7a. Here, the die original position refers to the lower end position of the punch 7b in a state where the die 7a and the punch 7b are in contact with each other.

Thus, the pinch position can be obtained by: obtaining the die original position by detecting the lower end position of the punch 7b in the state where the die 7a and the punch 7b are in contact with each other with the D-axis encoder 16 in advance; and detecting the position at which the lower end of the punch 7b is assumed to come into contact with the upper surface of the workpiece W with the D-axis encoder 16.

The final depth ST of the punch 7b is a position to which the punch 7b is lowered from the pinch position and at which the bending is finished.

First, in step 101 in FIG. 4 after the operation mode shifts to a punch final depth detection mode, machining simulation of materials (workpieces) is performed, and an influence coefficient of each material is calculated.

Specifically, predetermined dies and workpieces with predetermined thicknesses are selected, and machining simulation is performed using the workpieces having m different stress-strain relationships to calculate load F and largest strain $\epsilon$ at each of i stroke positions $S_i$ for each material based on the equations below. Note that the load F and the largest strain $\epsilon$ at each of the i stroke positions $S_i$ may be calculated and stored in the database 19 in advance, and the data may be obtained by referring to this database 19.

$$F_{mi}=f(S_i)$$

$$\{F_{mi},S_i\}$$

$$\epsilon_{mi}=f(S_i)$$

$$\{\epsilon_{mi},S_i\}$$

Subsequently, stress $\sigma_{mi}$ is calculated for each largest strain $\epsilon$ based on the equation below from the above stress-strain relationship of the corresponding material.

$$\sigma_{mi}=f(\epsilon_{mi})$$

$$\{\sigma_{mi},\epsilon_{mi}\}$$

With the stress-load relationship at each stroke calculated as described above, an influence coefficient $EC_i$ of the material is calculated based on the equation below.

$$EC_i = \frac{\sum_{j=1}^{m} F_{ji}\sigma_{ji}}{\sum_{j=1}^{m} F_{ji}^2}$$

Here, the above calculation process may be performed by causing the CPU 17 of the control device 9 to use the data on the punch and the die, the data on the product shape, and the data on the machining object (workpiece W) in the database 19 and also to use the RAM 15 based on the computer program from the ROM 13 by following the settings and instructions from the operator through the input-display unit 11. Alternatively, another computer may be connected to the control device 9, and this computer may perform the calculation process and transfer the data to the control device 9.

Then, in step 103, a reference depth is calculated from machining information on the workpiece and is set.

Specifically, the CPU 17 of the control device 9 calculates the reference depth (first target position) based on the data on the punch and die, the data on the product shape (such as the bend angle and the bend length), and the data on the machining object (workpiece W) (such as the thickness and the material) in the database 19. Here, the reference depth (first target position) is a final lowered position PD of the punch 7b in the bending as shown in FIG. 5, and is calculated by a generally used method based on the data on the punch and die, the data on the product shape (such as the bend angle and the bend length), and the data on the machining object (workpiece W) (such as the thickness and the material).

Then, in step 105, the operation mode shifts to a machining mode, and the thickness of the workpiece W to be machined is measured.

Specifically, the thickness of the workpiece W to be machined is measured with a generally used thickness measuring instrument, and the measured value is inputted through the input-display unit 11 and stored in a storage unit such as the RAM 15 or the database 19.

Then, in step 107, load applied to the punch 7b is measured with the pressure sensor 12 during the machining.

Specifically, the load applied to the punch 7b during the machining is detected with the pressure sensor 12, and the detected value is inputted through the input-display unit 11 and stored in the storage unit such as the RAM 15 or the database 19.

Then, in step 109, the slide position of the punch 7b on the D axis is detected with the D-axis encoder 16 during the machining.

Specifically, the slide position of the punch 7b on the D axis during the machining is detected with the D-axis encoder 16, and the detected value is inputted through the input-display unit 11 and stored in the storage unit such as the RAM 15 or the database 19.

Then, in step 111, the upper surface position of the workpiece W is calculated based on the load applied to the punch 7b, which is detected by the pressure sensor 12, and the slide position of the punch 7b on the D axis, which is detected by the D-axis encoder 16.

Specifically, the CPU 17 of the control device 9 calculates an upper surface position $P_0$ of the workpiece W based on the detected value of the load applied to the punch 7b in the storage unit and the detected value of the slide position of the punch 7b on the D axis in the storage unit. Here, the upper surface position of the workpiece W refers to the position of the upper surface of the workpiece W placed on the die 7a, and is calculated by a generally used method based on the detected value of the load and the detected value of the slide position in the storage unit.

Then, in step 113, actual stroke amounts each of which is a distance by which the punch 7b has moved from the upper surface position $P_0$ of the workpiece W is calculated by sampling slide positions $P_i$ of the punch 7b on the D axis with the D-axis encoder 16.

Specifically, the CPU 17 of the control device 9 samples the slide positions $P_i$ detected with the D-axis encoder 16, and calculates actual stroke amounts $S_i$ by which the punch has actually moved from the detected material upper surface position $P_0$ based on the equation below.

$$S_i=P_0-P_i-M_i$$

where $M_i$ is the amount of warpage of the machine at each stroke position, and is calculated from the machine shape, the bend position, the bend length, and the load.

Then, in step 115, load $F_i$ applied to the punch 7b at each actual amount $S_i$ by which the punch has actually moved is detected with the pressure sensor 12, stress $\sigma_i$ is obtained from the load $F_i$ and the influence coefficient $EC_i$ of the material obtained in step 101, and then a material constant is obtained from the change in the stress $\sigma_i$.

Specifically, the CPU 17 of the control device 9 calculates the stress $\sigma_i$ based on the equation below from the load $F_i$ applied to the punch 7b at the actual stroke amount $S_i$ which is detected with the pressure sensor 12, and the influence coefficient $EC_i$ of the material obtained in advance.

$$\sigma_i = EC_i * F_i$$

Then, the CPU 17 of the control device 9 calculates the largest strains ε for the i stroke positions S from nominal material information in the workpiece information based on the equation below. This equation serves as a stroke-strain conversion equation (alternatively, data may be obtained by referring to the database).

$$\epsilon_i = f(S_i)$$

$$\{\epsilon_i, S_i\}$$

As a result, stress data for each strain is determined, material characteristics as described below are obtained, and the material constant is obtained from these material characteristics.

$$\{\sigma_i, \epsilon_i\}$$

Then, in step 117, the final depth of the punch (second target position) is calculated based on the data on the punch and the die, the data on the product shape (such as the bend angle and the bend length), the data on the machining object (workpiece W) (such as the thickness and the material), and the measured thickness and the material constant of the workpiece W.

Specifically, the CPU 17 of the control device 9 obtains the curvature of the material in the die to obtain the bent shape of the material from an equilibrium equation for an external moment generated due to the effect of the machining force and an internal bending moment generated inside the workpiece and calculated from the material constant, based on the data on the punch and the die, the data on the product shape (such as the bend angle and the bend length), the data on the machining object (workpiece W) (such as the thickness and the material), and the measured thickness and the material constant of the workpiece W. Then, the CPU 17 of the control device 9 calculates the final depth of the punch (second target position).

Then, in step 119, the punch is lowered until reaching the value of the final depth of the punch (second target position) to bend the workpiece W.

As described above, according to this embodiment, even if the material characteristics vary from one workpiece to another, the workpiece W of interest is bent by correcting the final depth of the punch according to the variation in the material characteristics of the workpiece. Thus, accurate bending is possible.

This invention is not limited to the embodiment of the invention described above, but is capable of being carried out in other manners by making appropriate changes as below.

Next, another embodiment of the invention of the present application will be described with reference to FIGS. 6 to 12.

Figure 6:
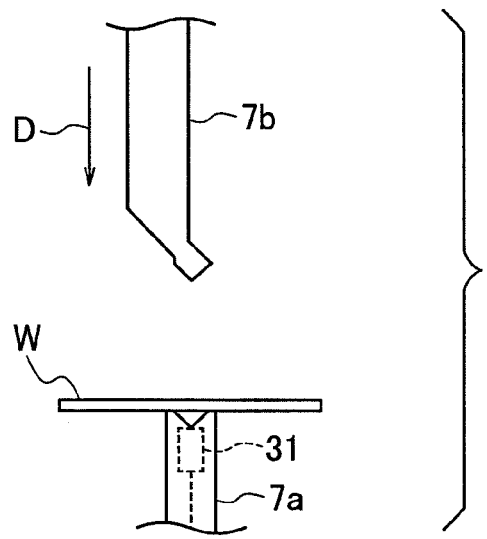
FIG. 6 is a schematic view of a part around a die and a punch in another embodiment of the machine tool (bending machine) of the present invention.
Figure 7:
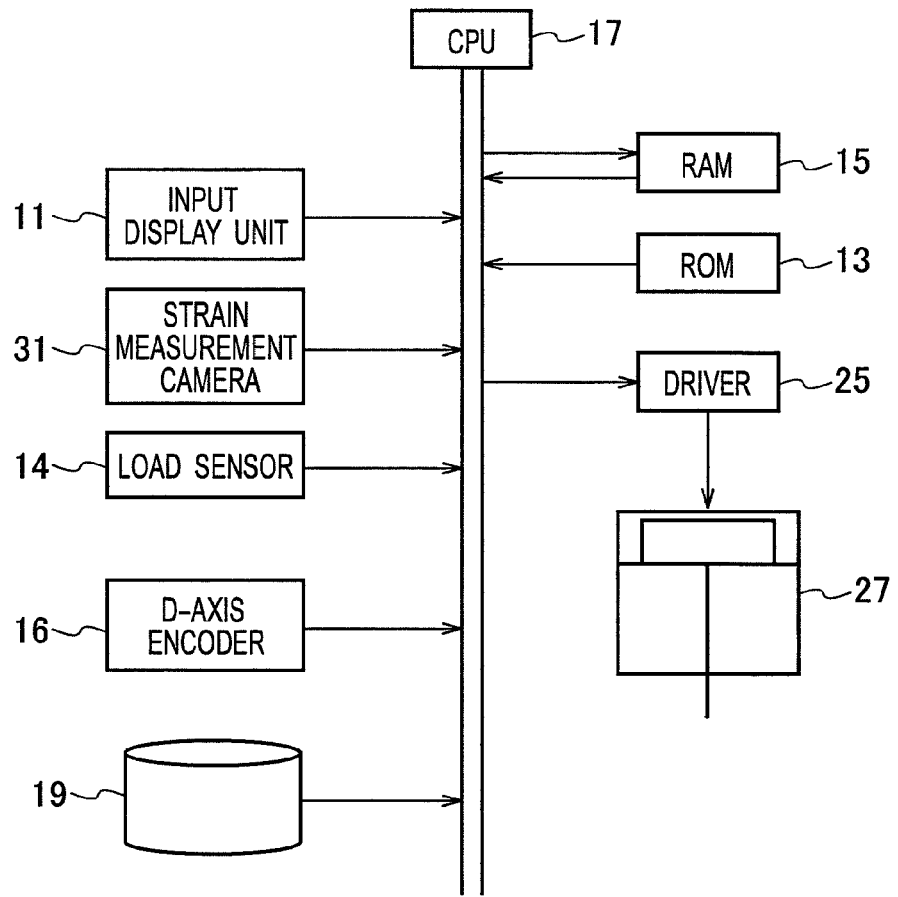
FIG. 7 is a block diagram showing the schematic configuration of a control device 9 of a bending machine 7 in the other embodiment shown in FIG. 6.

FIG. 6 is a schematic view of a part around a die and a punch in another embodiment of the invention of the present application. FIG. 7 is a block diagram showing the schematic configuration of a control device 9 of a bending machine in the other embodiment of the invention of the present application.

As in the first embodiment shown in FIG. 1, this machine tool (bending machine) 7 is configured to bend a workpiece W (material) fed between a die 7a and a punch 7b with the die 7a and the punch 7b by sliding the punch 7b in a D-axis direction D (see FIG. 6) relative to the die 7a. The die 7a is provided to a lower part as a first bending tool, whereas the punch 7b is provided to an upper part as a second bending tool.

Moreover, as shown in FIGS. 6 and 7, this bending machine 7 is provided with: a load sensor 14 (shown in FIG. 7) provided to an upper portion of the punch 7b and configured to detect load pressure applied to the workpiece W; and a D-axis encoder 16 (shown in FIG. 3) provided to the upper portion of the punch 7b and configured to detect the slide position of the punch 7b on the D axis.

Further, as shown in FIG. 6, a strain measurement camera 31 is provided in an upper portion of the die 7a at a position facing the tip of the punch 7b, and is configured to measure strain at a particular portion of the workpiece W (X in FIG. 9) on the opposite side from the upper surface of the workpiece W at a position which the tip of the punch 7b comes into contact with.

Furthermore, the bending machine 7 includes the control device 9 responsible for the control on the whole machine tool. This control device 9 is provided with an input-display unit 11 configured to display predetermined images and receive instructions from the operator.

In addition, under control of the control device 9, the workpiece is bent in accordance with bending operation inputted and set through the input-display unit 11. In this example, the final position of the punch (the position to which the punch is finally pushed in or the final depth of the punch) to be described later is detected, and the bending is performed by this corrected final position thus detected.

As shown in FIG. 7, the control device 9 of the bending machine 7 includes a CPU 17 to which a ROM 13 and a RAM 15 are connected through a bus, and the load sensor 14, the input-display unit 11 serving as both an input unit and a display unit, the D-axis encoder 16, a database 19, and the strain measurement camera 31 are also connected to the CPU 17 through the bus.

Moreover, a driver 25 configured to drive a cylinder 27 configured to vertically drive an upper table equipped with the punch 7b is also connected to the CPU 17 through the bus.

In this example, the CPU 17 is configured to detect the final position of the punch (the final depth of the punch) as described later and also perform the inputted and set bending operation by using data on the punch and the die, data on the product shape, and data on the machining object (workpiece W) in the database 11 and also using the RAM 15 based on a computer program from the ROM 13 in accordance with settings and instructions from the operator through the input-display unit 11.

Next, punch final position detection operation will be described with reference to FIGS. 8 to 12.

Figure 8:
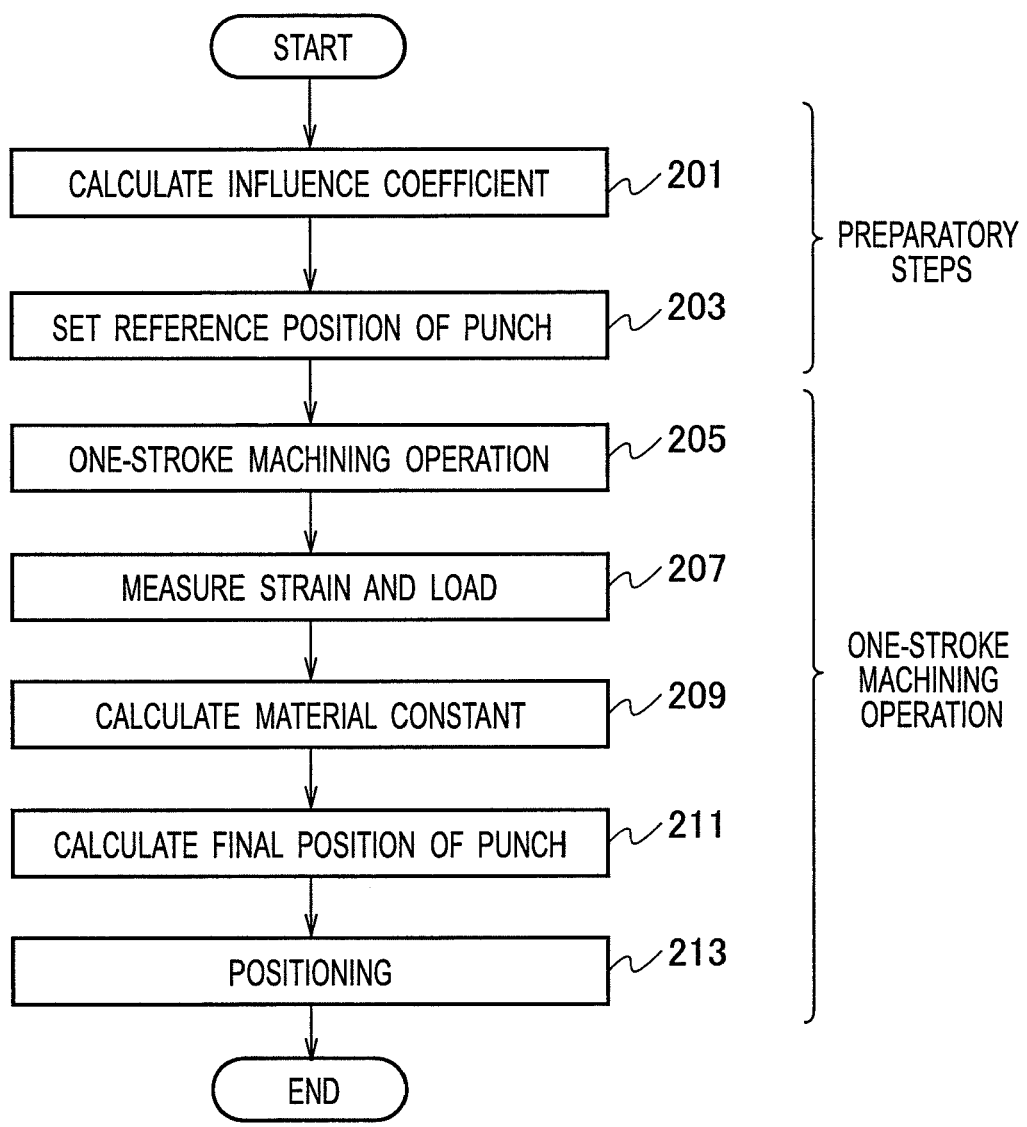
FIG. 8 is a flowchart of an operation in the other embodiment shown in FIG. 6.

FIG. 8 is a flowchart of the punch final position detection operation in the other embodiment of the invention of the present application, and is an explanatory chart of the punch final position detection operation in the other embodiment of the invention of the present application.

Note that the CPU 17 performs this punch final position detection operation by using the RAM 15 based on the computer program from the ROM 13 as mentioned above.

The main features of the punch final position detection operation in the other embodiment of the invention of the present application are as follows.

Material characteristics of a machining object (workpiece) to be actually machined have actual values and nominal values which differ from each other. These differences are distinguished as a nominal thickness t, nominal material characteristics (stress-strain data or a plasticity coefficient: C and a strain hardening index: n), an actual thickness t', and actual material characteristics (stress-strain data or a plasticity coefficient: C' and a strain hardening index: n' of a particular material). During a machining operation, the control device 9 determines the actual material characteristics and re-calculates an optimal operation target value (the final position of the punch) for the material. Then, the machining operation is performed based on the final position of the punch thus re-calculated. In this way, it is possible to prevent angle variations due to the material variations.

In this example, assuming machining using particular dies and nominal thickness, nominal material characteristics (the stress-strain data value or nominal plasticity coefficient: C and the nominal strain hardening index: n) of m kinds of materials (e.g. SPCC, SPHC, SUS304, SUS430, A1100, A5052, etc.), a nominal thickness t, and die information are used to calculate load and strain at a particular portion during machining for each material. By using these pieces of information, an equation (or database) indicating the relation between stress and machining load is created. By using this equation (or database) and based on the load-strain relationship or the load-stroke relationship in the machining of the actual material (unknown material), the stress-strain relationship of the material being machined is predicted.

Now, a final position $D_F$ of the punch 7b (see FIG. 11) will be described. First of all, a pinch position refers to a position at which the workpiece W is clamped by the die 7a and the punch 7b. More specifically, the pinch position is equivalent to the distance from a die original position to the lower end of the punch 7b in a state where the lower end of the punch 7b is in contact with the upper surface of the workpiece W with the thickness t placed on the die 7a. Here, the die original position refers to the lower end position of the punch 7b in a state where the die 7a and the punch 7b are in contact with each other.

Thus, the pinch position can be obtained by: obtaining the die original position by detecting the lower end position of the punch 7b in the state where the die 7a and the punch 7b are in contact with each other with the D-axis encoder 16 in advance; and detecting the position at which the lower end of the punch 7b is assumed to come into contact with the upper surface of the workpiece W with the D-axis encoder 16.

Moreover, the final position $D_F$ of the punch 7b is a final position to which the punch 7b is lowered from the pinch position and at which the bending is finished.

In step 201 in FIG. 8, as a preparatory step, machining simulation of materials (workpieces) is performed, and an approximate equation of the relationship between stress and machining load of each material is obtained.

This approximate equation of the relationship between stress and machining load of the material is calculated using an external calculation device in advance for faster prediction calculation of a material constant. The material constant can be predicted in a shorter period of time during machining by calculating the approximate equation of the relationship between stress and machining load of the material in advance as described above.

Note that the control device 9 may instead calculate the approximate equation of the relationship between stress and machining load of the material.

Next, the content of the calculation of the approximate equation of the relationship between stress and machining load of the material will be described.

Generally, material characteristics M in plastic deformation are described by the relationship between stress σ and strain ε of the material, and this information can be obtained by a tensile test.

$$\{\epsilon_i, \sigma_i\} \quad (1)$$

An approximate equation of this stress-strain data is the equation below.

$$\sigma = C\epsilon^n \quad (2)$$

(here, the plasticity coefficient: C and the strain hardening index: n will be collectively denoted by M as parameters representing the material characteristics)

Note that approximation using a primary expression $\sigma = a\epsilon + Y$ is possible as an alternative (here, a and Y may be collectively denoted by M as parameters representing the material characteristics).

Figure 9:
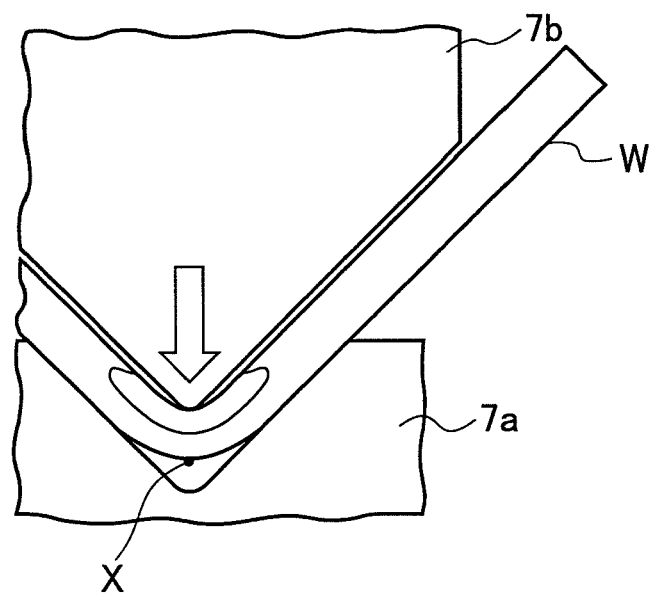
FIG. 9 is an explanatory view of the operation in the other embodiment shown in FIG. 6.
Figure 9:
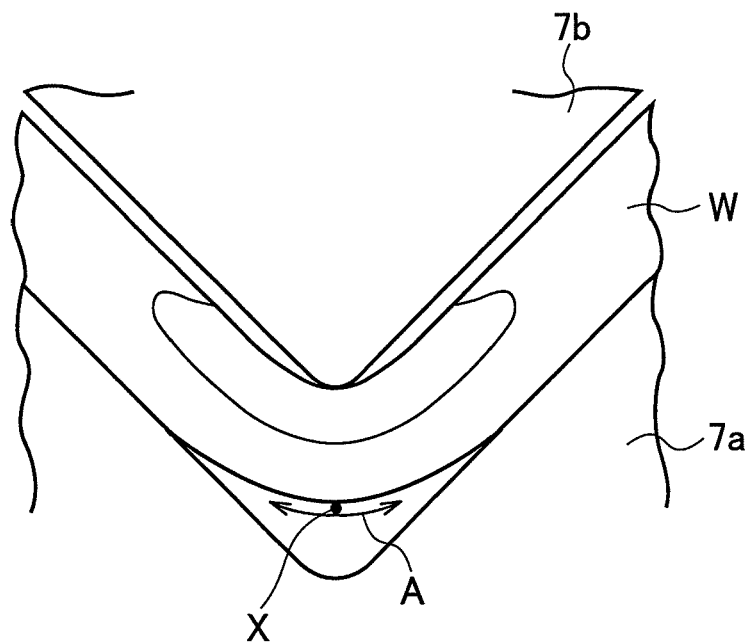

Moreover, the external calculation device is used to calculate strain $\epsilon_X$ at a particular portion X from machining load F (per unit bend length) by using FEM (machining simulation by a finite element method) as shown in FIG. 9 based on particular die information, nominal thickness information t, and the material characteristics M (the plasticity coefficient: C and the strain hardening index: n or the stress-strain data $\{\sigma_i, \epsilon_i\}$) (note that plastic dynamics calculation may used instead).

Here, as shown in FIG. 9, the particular portion X is a particular portion of the workpiece W on the opposite side from the upper surface of the workpiece W at a position which the tip of the punch 7b comes into contact with.

$$\epsilon_X = f(\text{tool}, t, M, F) \quad (3)$$

Here, in the case the machining model involves the machining load F and the strain $\epsilon_X$ at the particular portion X, the detection is easier and the measurement accuracy is therefore higher if the particular portion X is a portion where the strain is larger (the lowermost layer immediately below the punch, for example). Thus, the particular portion X is not particularly limited to a specific position as long as it is at a point (including multiple points or regions) which can be calculated and also measured or predicted during the subsequent machining stroke.

Note that in this step 201, m kinds of materials are selected. They are selected as representative materials from a group of materials each of which has a possibility of being chosen as an unknown material to be finally subjected to the prediction. The larger the number, the more the samples of the subsequent approximation calculation, and therefore the higher the prediction accuracy.

A tensile test is performed on these materials to measure the relationship between the stress σ and the strain ε for each of the m kinds.

$$\{\epsilon_{mi}, \sigma_{mi}\} \quad (5)$$

For this stress-strain data, the approximate equation (power approximation) is the equation below for each of the m kinds of materials.

From (2), $$\sigma_m = C_m \epsilon^{n_m} \quad (6)$$

(here, a plasticity coefficient: $C_m$ and a strain hardening index: $n_m$ will be collectively denoted by $M_m$ as parameters representing the material characteristics of the material m).

Note that approximation using a primary expression $\sigma_m = a_m \epsilon + Y_m$ is possible as an alternative (here, $a_m$ and $Y_m$ may be collectively denoted by $M_m$ as parameters representing the material characteristics of the material m).

Moreover, strain $\epsilon_{Xm}$ at the particular portion X of each of the m kinds of materials is obtained based on the machining model (3). From (3), $$\epsilon_{Xm} = f(\text{tool}, t, M_m, F) \tag{7}$$

is obtained, which, with the strain $\epsilon_X$, is converted into the equation below for obtaining machining load $F_m$ of each of the m kinds of materials.

$$F_m = f^{-1}(\text{tool}, t, M_m, \epsilon_X) \tag{8}$$

Then, assuming that the strain by the bending is a uniaxial strain in the circumferential direction, the relationship between the strain $\epsilon_X$ at the particular portion X in the circumferential direction and the stress at that position in the circumferential direction is described by the equation below.

$$\sigma_{Xm} = C_m \epsilon_X^{n_m} \tag{9}$$

Here, the strain $\epsilon_X$ at the particular portion X in the course of the machining stroke can be expressed as $\epsilon_{Xi}$ as below.

$$\downarrow \epsilon X_0$$

$$\downarrow \epsilon X_1$$

$$\downarrow \epsilon X_2$$

.

$$\downarrow \epsilon X_i$$

From (8), the following is obtained.

$$\{\epsilon_{Xi}, F_{mi}\} \tag{10}$$

(note that this data may be obtained by performing the actual machining and measuring the machining load F and the strain at the particular portion in a test)

From (9), $$\{\epsilon_{Xi}, \sigma_{Xmi}\} \tag{11}$$

From (10) and (11), the relationship between the stress $\sigma_{Xmi}$ and the machining load $F_{mi}$ in the case where the strain is $\epsilon_{Xi}$ is obtained.

$$\{\sigma_{Xmi}, F_{mi}\} \tag{12}$$

An approximate equation is created for the relationship between the stress $\sigma_{Xmi}$ and the machining load $F_{mi}$ of the m kinds of materials for each of the i strains $\epsilon_{Xi}$, so that i approximate equations are created. Thus, a relational equation of the stress and the machining load which is not dependent on the material can be created for each strain $\epsilon_{Xi}$.

$$\sigma_{Xi} = f_i(F) \tag{13}$$

By calculating the approximate equations before the machining, the stress-strain relationship (material constant) can be obtained from strain $\epsilon'_{Xi}$ and machining load $F'_i$ at each of i particular positions on an unknown material which are obtained during the machining in the following steps.

Figure 10:
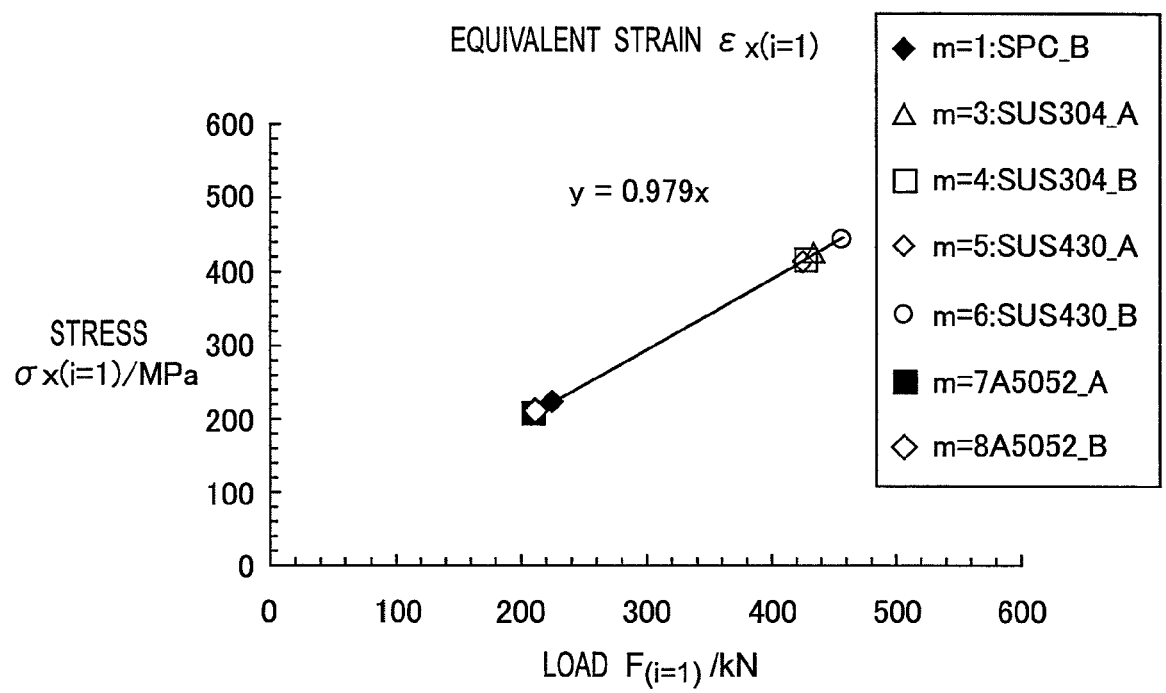
FIG. 10 is a graph for describing the operation in the other embodiment shown in FIG. 6.

Note that FIG. 10 shows a specific example of the stress-strain relationship obtained from the strain $\epsilon'_{Xi}$ and the machining load $F'_i$ at each particular position on various materials.

The calculation time taken to obtain this equation (13) is several hours because the calculation time for one material in a particular machining model (0.1 to 1 H)×m kinds of materials in the case of FEM. For this reason, performing these calculations in advance is effective compared to performing the calculations during machining.

In the future, however, the calculation time will be shorter, and it may therefore be possible to perform the calculations including "the calculation of the material constant prediction equations" in the internal calculation device during machining.

Then, in step 203 in FIG. 8, a reference position (reference depth) $D_o$ of the punch 7b is set.

Figure 11:
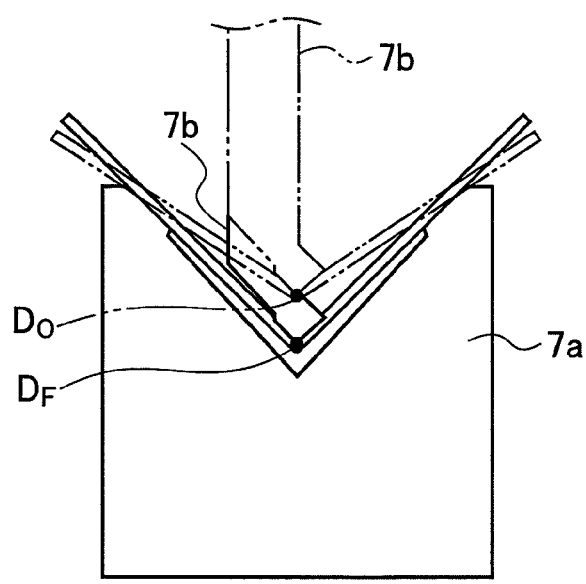
FIG. 11 is an explanatory view of the operation in the other embodiment shown in FIG. 6.

Specifically, a predetermined position is calculated based on machining information on the workpiece such as the nominal thickness, the nominal material characteristics (the average value of the stress-strain data, the nominal plasticity coefficient: C, and the strain hardening index: n), punch information, die information, bend angle, and bend length. Then, as shown in FIG. 11, a position which is before the predetermined position by a certain distance is set as the reference position (first target position) $D_o$. Note that the method of setting this reference position (first target position) $D_o$ is described specifically in Japanese Patent Application Publication No. Hei 8-24955 (paragraphs 0036, 0037, etc., in which the reference position is described as a table shifting position), and is therefore not described here.

These steps 201 and 203 are the preparatory steps.

Then, in step 205 in FIG. 8, one-stroke machining operation is started with the reference position (first target position) as a target value. In step 207, the strain at the particular portion and the machining load during this one-stroke machining operation are measured.

Specifically, as described below, the actual machining load $F'_i$ for the strain $\epsilon'_{Xi}$ at each particular position is measured with the strain measurement camera 31 and the load sensor 14, and $F'_i$ is converted to a load per unit bend length.

Hereinafter, each variable with ' represents an actually measured value obtained when the unknown material is machined.

$$\{\epsilon'_{Xi}, F'_i\} \tag{14}$$

Then, in step 209, the material constant is calculated.

Specifically, first, during the machining, the machining load for each strain during the machining is measured with the strain measurement camera 31 set inside the die 7a and the load sensor 14. Based on the equations (13) and (14), the stress-strain relationship (material constant) is calculated from the approximate equation below.

$$\{\sigma'_i, \epsilon'_i\} \tag{15}$$

From (16), this approximate equation of the stress-strain data is $$\sigma = C' \epsilon^{n'} \tag{16}$$

(here, the plasticity coefficient: C' and the strain hardening index: n' will be collectively denoted by M' as parameters representing the material characteristics).

Note that approximation using a primary expression $\sigma = a'\epsilon + Y'$ is possible as an alternative (a' and Y' may be collectively denoted by M' as parameters representing the material characteristics).

Then, in step 211, the final position $D_F$ of the punch 7b is calculated.

Specifically, as shown in FIG. 11, the final positioning position $D_F$ is calculated from information such as the actual thickness, the nominal thickness, the material constant calculated from the equations (15) and (16) (the stress-strain data value, the actual plasticity coefficient: C', and the actual strain hardening index: n'), the punch information, the die information, the bend angle, and the bend length.

Note that the method of calculating this final positioning position $D_F$ is described specifically in Japanese Patent Application Publication No. 2000-140943, and is therefore not described here.

Then, in step 213, the punch 7b is moved and positioned to the final position of the punch 7b calculated in step 211.

These steps 205 to 213 are the one-stroke machining operation.

Note that the actual machining operation of the workpiece (material) is performed based on the final position of the punch 7b positioned as described above.

A specific example carried out in accordance with the other embodiment of the invention of the present application will be described below with reference to a graph in FIG. 12.

Figure 12:
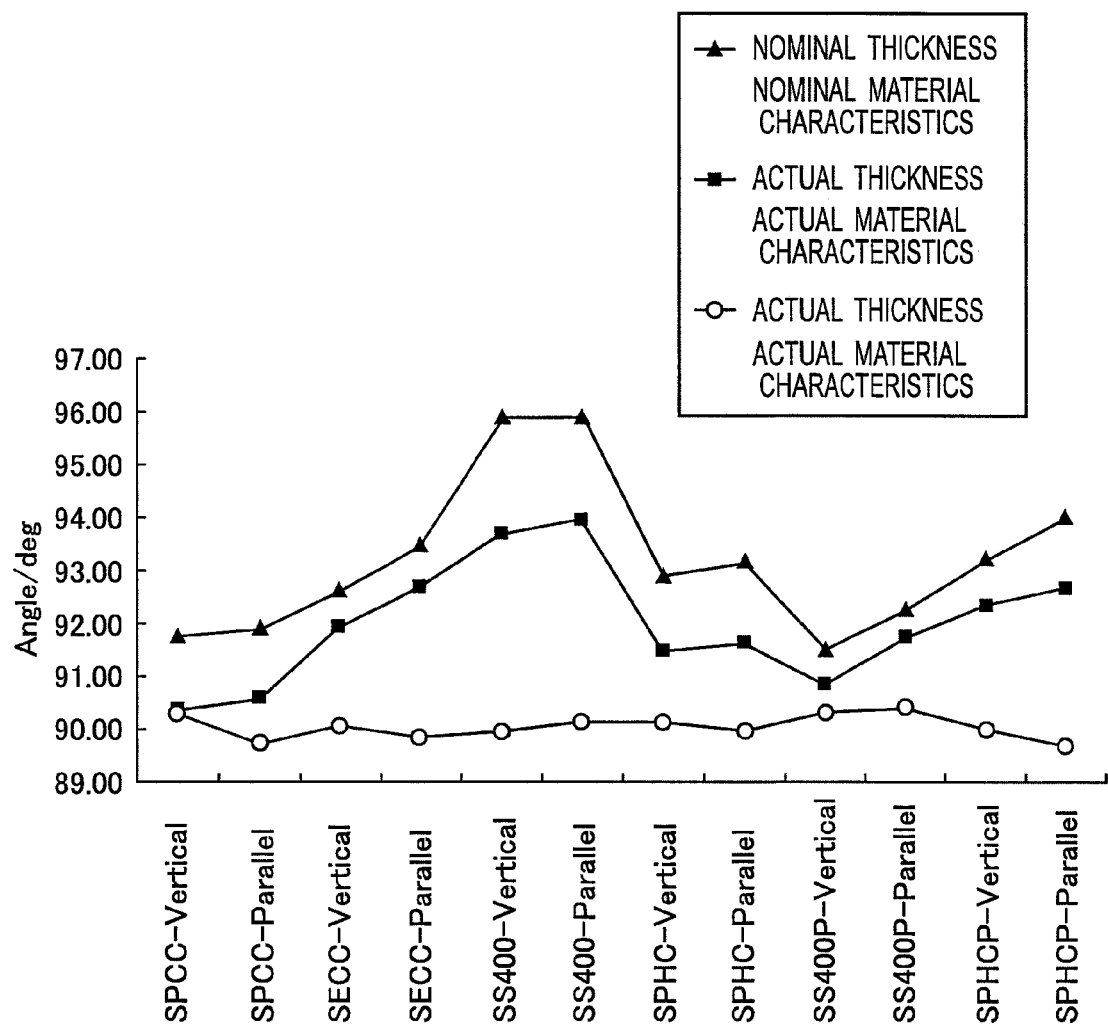
FIG. 12 is a graph for describing the operation in the other embodiment shown in FIG. 6.

The graph in FIG. 12 shows the result of measurement obtained by bending each of steel materials with a nominal thickness of 3.2 mm at a target angle of 90° and measuring the angle.

SPCC, SECC, SS400, SPHC, pickled SS400, and pickled SPHC are prepared as unknown steel materials, and the bend angles of these sheets machined in bending directions which are perpendicular and parallel to their rolled direction are measured.

In FIG. 12, ▲ represents an angle of the material machined by the same final depth as that calculated from the nominal thickness and the nominal material (which is the same for all the steel materials); ■ represents the angle of the material machined by a different final depth calculated from the actually measured thickness of the material and the nominal material (which is the same for all the steel materials); and ○ represents the angle of the material machined by a final depth calculated from the actually measured thickness of the material and the actual material characteristics obtained by predicting the stress-strain relationship of the material in accordance with the technique of this invention. ▲ indicates a variation of 95.91 to 91.51 for the target angle 90°, ■ indicates a variation of 93.98 to 90.4 for the target angle 90°, and ○ indicates a variation of 90.41 to 89.7 for the target angle 90°.

This graph indicates that the variation and absolute accuracy error are both reduced by individually predicting the actual thickness and the actual material characteristics, thus showing the effect of obtaining the final depth via the prediction of the actual thickness and the actual material characteristics.

Moreover, in the case where the thickness of an unknown material to be machined is a thickness (actual thickness) different from the nominal thickness, it is also possible to measure the actual thickness t' of the material with a thickness measuring instrument before the machining (between steps 203 and 205) or measure the actual thickness t' of the material in advance with a vernier scale, a micrometer, or the like and use this actual thickness in place of the nominal thickness in the calculation of the final position. In this way, the prediction accuracy can be further enhanced. Moreover, it is also possible to calculate it from the pinch position, the die original position, and the die parameters.

INDUSTRIAL APPLICABILITY

According to the present invention, even when material characteristics vary from one workpiece to another, a workpiece can be accurately bent by correcting the final depth of the punch in accordance with the variation in the material characteristics of the workpiece.

The invention claimed is:

1. A machine tool having a control device for bending a workpiece by clamping the workpiece with first and second bending tools under the control of the control device, wherein the control device is configured to, as preparation prior to the bending of the workpiece:

obtain a relationship between stress and strain of each of a plurality of kinds of workpieces by performing a material test thereon, obtain a relationship between strain and machining load at a particular portion of each of the workpieces by calculating a machining model which is based on the workpiece with use of the relationship between the stress and the strain, and calculate a relational equation of the machining load and stress of a workpiece of the plurality of kinds of workpieces, and after the preparation, the control device is further configured to:

obtain, as a material constant, a relationship between stress and strain of the workpiece to be bent based on the relational equation of the machining load and the stress and values of the strain and machining load of the workpiece to be bent, calculate, prior to completing a bending operation of the workpiece, a final bending position of the second bending tool based on the material constant and a machining condition, and complete bending of the workpiece based on the final position of the second bending tool.

2. The machine tool according to claim 1, wherein the obtaining of the relationship between the stress and the strain of the workpiece to be bent as the material constant includes:

setting a reference position of the second bending tool;

measuring the strain at the particular portion and the machining load during the bending operation; and calculating a material constant which is based on the relationship between the stress and the strain of the workpiece to be bent, from the measured values of the strain at the particular portion and the machining load and an approximate equation of the relationship between the machining load and the stress of the workpiece.

3. The machine tool according to claim 1, wherein the obtaining of the relationship between the stress and the strain of the workpiece to be bent as the material constant includes:

setting a reference position of the second bending tool;

measuring a stroke and the machining load during the bending operation;

obtaining a value of the strain at the particular portion of the workpiece to be bent from a stroke-strain conversion equation; and calculating the material constant which is based on the relationship between the stress and the strain of the workpiece to be bent, from values of the strain at the particular portion and the machining load and an approximate equation of the relationship between the machining load and the stress of the workpiece.

4. A machine tool having a control device for bending a workpiece by clamping the workpiece with first and second bending tools under control of the control device, wherein the control device is configured to:

distinguish a material characteristic of the workpiece as an actual value and a nominal value;

determine an actual material characteristic during a machining operation and re-calculates an optimal operation target value for the workpiece; and bend the workpiece by operating any one of the first bending tool and the second bending tool in accordance with the optimal operation target value thus re-calculated.

* * * * *